United States Patent
Howard et al.

(10) Patent No.: US 10,677,343 B2
(45) Date of Patent: Jun. 9, 2020

(54) FLUID DISTRIBUTION ASSEMBLY HAVING ANTI-CLOG INLET HOUSING

(71) Applicant: SIKORSKY AIRCRAFT CORPORATION, Stratford, CT (US)

(72) Inventors: Bertrand J. Howard, Shelton, CT (US); Eric James Hodgkinson, New Hartford, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 211 days.

(21) Appl. No.: 15/549,237

(22) PCT Filed: Feb. 10, 2016

(86) PCT No.: PCT/US2016/017379
§ 371 (c)(1),
(2) Date: Aug. 7, 2017

(87) PCT Pub. No.: WO2016/133761
PCT Pub. Date: Aug. 25, 2016

(65) Prior Publication Data
US 2018/0031107 A1    Feb. 1, 2018

Related U.S. Application Data

(60) Provisional application No. 62/117,507, filed on Feb. 18, 2015.

(51) Int. Cl.
*F16H 57/04*    (2010.01)
*B64C 27/12*    (2006.01)
(Continued)

(52) U.S. Cl.
CPC ......... *F16H 57/0404* (2013.01); *B64C 27/12* (2013.01); *B64D 33/00* (2013.01);
(Continued)

(58) Field of Classification Search
CPC ..... F16H 57/0404; B64C 27/12; B64C 27/04; F01M 1/10; F01M 11/0004; F01M 11/02;
(Continued)

(56) References Cited

U.S. PATENT DOCUMENTS 1,742,758 A * 1/1930 Curphey ............. F04B 53/1037
184/6.24
2,548,160 A * 4/1951 Hunter .................... F01M 1/10
184/6.24
(Continued)

FOREIGN PATENT DOCUMENTS

DE    19735444 A1    1/1999
FR    2989444 A3    10/2013

OTHER PUBLICATIONS

FR2989444—Machine Translation (Year: 2013).*
(Continued)

*Primary Examiner* — Michael A Riegelman
(74) *Attorney, Agent, or Firm* — Cantor Colburn LLP

(57) ABSTRACT

A fluid distribution assembly for distributing a fluid, the fluid distribution assembly includes an inlet housing including a first conduit and a bypass conduit; a chip detector cavity in fluid communication with the first conduit such that the fluid can pass through the first conduit into the chip detector cavity; and an outlet housing in fluid communication with the chip detector cavity and the bypass conduit such that the fluid can pass into the outlet housing through the chip detector cavity and/or the bypass conduit.

15 Claims, 5 Drawing Sheets

(51) Int. Cl.
*G01N 33/28* (2006.01)
*F01M 1/10* (2006.01)
*F01M 11/00* (2006.01)
*B64D 33/00* (2006.01)
*F16N 39/06* (2006.01)
*F01M 11/02* (2006.01)

(52) U.S. Cl.
CPC .......... *F01M 1/10* (2013.01); *F01M 11/0004* (2013.01); *G01N 33/2888* (2013.01); *F01M 11/02* (2013.01); *F01M 2001/1007* (2013.01); *F01M 2001/1057* (2013.01); *F01M 2001/1078* (2013.01); *F01M 2011/005* (2013.01); *F01M 2011/007* (2013.01); *F01M 2011/0029* (2013.01); *F16N 39/06* (2013.01); *F16N 2039/065* (2013.01); *F16N 2210/08* (2013.01); *F16N 2250/30* (2013.01)

(58) Field of Classification Search
CPC ... F01M 2001/1007; F01M 2001/1078; F01M 2011/0029; F01M 2001/005; F01M 2011/007; G01N 33/2888; F16N 39/06; F16N 2039/065; F16N 2210/08; F16N 2250/30
See application file for complete search history.

(56) References Cited

U.S. PATENT DOCUMENTS

| | | | | |
|---|---|---|---|---|
| 3,817,380 | A * | 6/1974 | Brown | B01D 35/06 210/131 |
| 4,244,279 | A * | 1/1981 | Stewart | F04B 1/0408 60/456 |
| 4,429,587 | A * | 2/1984 | Finn, III | F16H 57/0447 184/6.12 |
| 4,707,165 | A | 11/1987 | Tauber et al. | |
| 5,121,599 | A * | 6/1992 | Snyder | F01D 25/20 184/6.11 |
| 5,411,116 | A | 5/1995 | Kish et al. | |
| 6,116,272 | A * | 9/2000 | Kratzet | F01M 1/16 137/516.11 |
| 8,226,822 | B2 * | 7/2012 | Paradise | F01D 25/18 210/167.04 |
| 8,708,105 | B2 * | 4/2014 | Sowul | F16H 57/0426 184/11.1 |
| 9,683,652 | B2 * | 6/2017 | Poster | B64C 27/12 |
| 2008/0116009 | A1 * | 5/2008 | Sheridan | F01D 25/18 184/6.4 |
| 2009/0183950 | A1 | 7/2009 | Brouillet et al. | |
| 2010/0025159 | A1 | 2/2010 | Gmirya et al. | |
| 2013/0323015 | A1 * | 12/2013 | DeWald | B60K 17/344 415/1 |
| 2015/0129361 | A1 * | 5/2015 | Hodgkinson | G01N 33/2888 184/6.4 |
| 2017/0254406 | A1 * | 9/2017 | Hodgkinson | F16N 29/02 |
| 2017/0363529 | A1 * | 12/2017 | Ture | G01N 15/0656 |
| 2018/0031107 | A1 * | 2/2018 | Howard | G01N 33/2888 |
| 2018/0066552 | A1 * | 3/2018 | Waddleton | B01D 29/44 |
| 2018/0086444 | A1 * | 3/2018 | Poster | B64C 27/14 |
| 2018/0087656 | A1 * | 3/2018 | Poster | F16H 57/02 |

OTHER PUBLICATIONS

PCT/US2016/017379, ISR/WO, dated Apr. 11, 2016, 12 pages.
Extended European Search Report; EP 16752819; dated Oct. 17, 2018; 7 pages.

* cited by examiner

FLUID DISTRIBUTION ASSEMBLY HAVING ANTI-CLOG INLET HOUSING

CROSS REFERENCE TO RELATED APPLICATIONS

This application is a National Stage application of PCT/US2016/017379, filed Feb. 10, 2016, which claims the benefit of U.S. Provisional Patent Application No. 62/117,507, filed Feb. 18, 2015, both of which are incorporated by reference in their entirety herein.

BACKGROUND

The subject matter disclosed herein relates generally to fluid distribution, and in particular, to a lubricant distribution assembly that having an anti-clog inlet housing for distributing lubricant in a rotary wing aircraft.

Existing rotary wing aircraft employ a lubricant distribution assembly to convey lubricant to one or more gearboxes. An existing lubricant distribution assembly has a single inlet housing with a chip detector sensor and chip detector screen. The chip detector sensor and chip detector screen capture and detect contaminants in the lubricant that is traveling to the lubricant pumps. A drawback to the existing lubricant distribution assembly is that excessive debris may clog the chip detector screen or the inlet housing and prevent lubricant from passing through the inlet housing to the lubricant pumps.

SUMMARY

In one exemplary embodiment, a fluid distribution assembly for distributing a fluid, the fluid distribution assembly includes an inlet housing including a first conduit and a bypass conduit; a chip detector cavity in fluid communication with the first conduit such that the fluid can pass through the first conduit into the chip detector cavity; and an outlet housing in fluid communication with the chip detector cavity and the bypass conduit such that the fluid can pass into the outlet housing through the chip detector cavity and/or the bypass conduit.

In addition to one or more of the features described above, or as an alternative, further embodiments could include a screen positioned between the first conduit and the bypass conduit, the screen to pass fluid between the first conduit and the bypass conduit.

In addition to one or more of the features described above, or as an alternative, further embodiments could include a filter in the chip detector cavity between the first conduit and the outlet housing.

In addition to one or more of the features described above, or as an alternative, further embodiments could include wherein when fluid flow through the first conduit and the chip detector cavity is unblocked, fluid flows in the first conduit, the chip detector cavity and the bypass conduit to the outlet housing.

In addition to one or more of the features described above, or as an alternative, further embodiments could include wherein when fluid flow through the first conduit or the chip detector cavity is blocked, fluid flows in the bypass conduit to the outlet housing.

In addition to one or more of the features described above, or as an alternative, further embodiments could include wherein the inlet housing includes an inlet; the inlet housing including a vortex reducer located adjacent the inlet which can reduce vortices created at an opening between the first conduit and the bypass conduit.

In addition to one or more of the features described above, or as an alternative, further embodiments could include wherein the vortex reducer includes a lip extending from one wall of the inlet housing towards the inlet.

In another exemplary embodiment, a rotary wing aircraft includes a rotor; a gearbox coupled to the rotor; an engine coupled to the gearbox; and a lubricant distribution system providing lubricant from a sump to the gearbox, the lubricant distribution system including an inlet housing including a first conduit and a bypass conduit; a chip detector cavity in fluid communication with the first conduit such that the fluid can pass through the first conduit into the chip detector cavity, the chip detector cavity housing a chip detector; and an outlet housing in fluid communication with the chip detector cavity and the bypass conduit such that the fluid can pass into the outlet housing through the chip detector cavity and/or the bypass conduit.

In addition to one or more of the features described above, or as an alternative, further embodiments could include a screen positioned between the first conduit and the bypass conduit, the screen passing fluid between the first conduit and the bypass conduit.

In addition to one or more of the features described above, or as an alternative, further embodiments could include a filter in the chip detector cavity between the first conduit and the outlet housing.

In addition to one or more of the features described above, or as an alternative, further embodiments could include wherein when fluid flow through the first conduit is unblocked, fluid flows in the first conduit and the bypass conduit to the outlet housing.

In addition to one or more of the features described above, or as an alternative, further embodiments could include wherein when fluid flow through the first conduit is blocked, fluid flows in the bypass conduit to the outlet housing.

In addition to one or more of the features described above, or as an alternative, further embodiments could include wherein the inlet housing includes an inlet; the inlet housing including a vortex reducer located adjacent the inlet.

In addition to one or more of the features described above, or as an alternative, further embodiments could include wherein the vortex reducer includes a lip extending from one wall of the inlet housing towards the inlet.

In addition to one or more of the features described above, or as an alternative, further embodiments could include a pump coupled to the outlet housing, the pump directing lubricant through inlet housing.

Other aspects, features, and techniques of the invention will become more apparent from the following description taken in conjunction with the drawings.

BRIEF DESCRIPTION OF THE DRAWINGS

Referring now to the drawings wherein like elements are numbered alike in the several FIGURES, in which.

DETAILED DESCRIPTION

Figure 1:
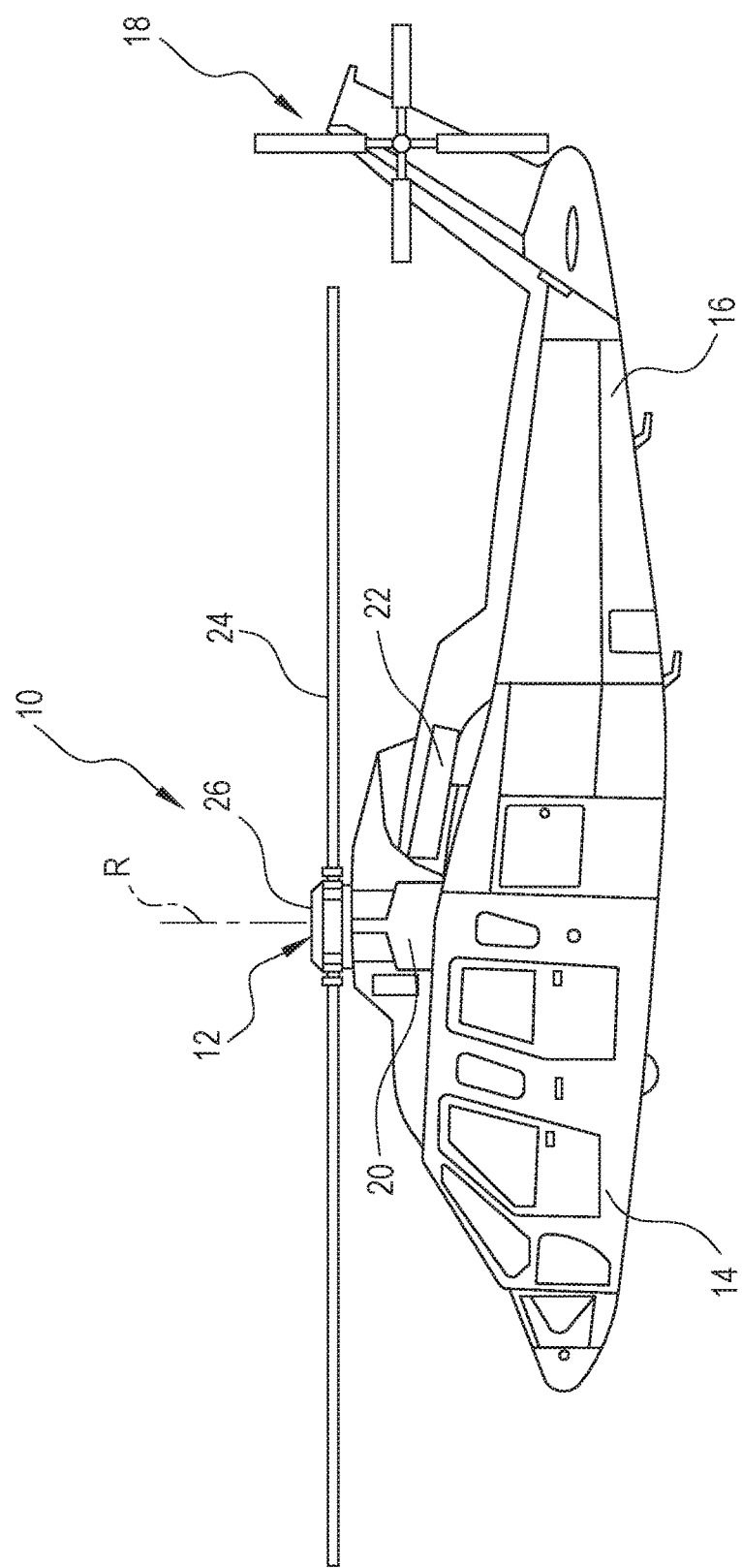
FIG. 1 illustrates a rotary wing aircraft in an exemplary embodiment.

FIG. 1 illustrates a rotary-wing aircraft 10 having a main rotor assembly 12. The aircraft 10 includes an airframe 14 having an extending tail 16, which mounts a tail rotor system 18, such as an anti-torque system, a translational thrust system, a pusher propeller, a rotor propulsion system, and the like. The main rotor assembly 12 is driven about an axis of rotation R through a main gearbox 20 by one or more engines 22. The main rotor assembly 12 includes a multiple of rotor blades 24 mounted to a rotor hub 26. Although a particular helicopter configuration is illustrated and described in the disclosed embodiment, other configurations and/or machines, such as high speed compound rotary wing aircraft with supplemental translational thrust systems, dual contra-rotating, coaxial rotor system aircraft, turbo-props, tilt-rotors and tilt-wing aircraft, will also benefit from embodiments of the invention.

Figure 2:
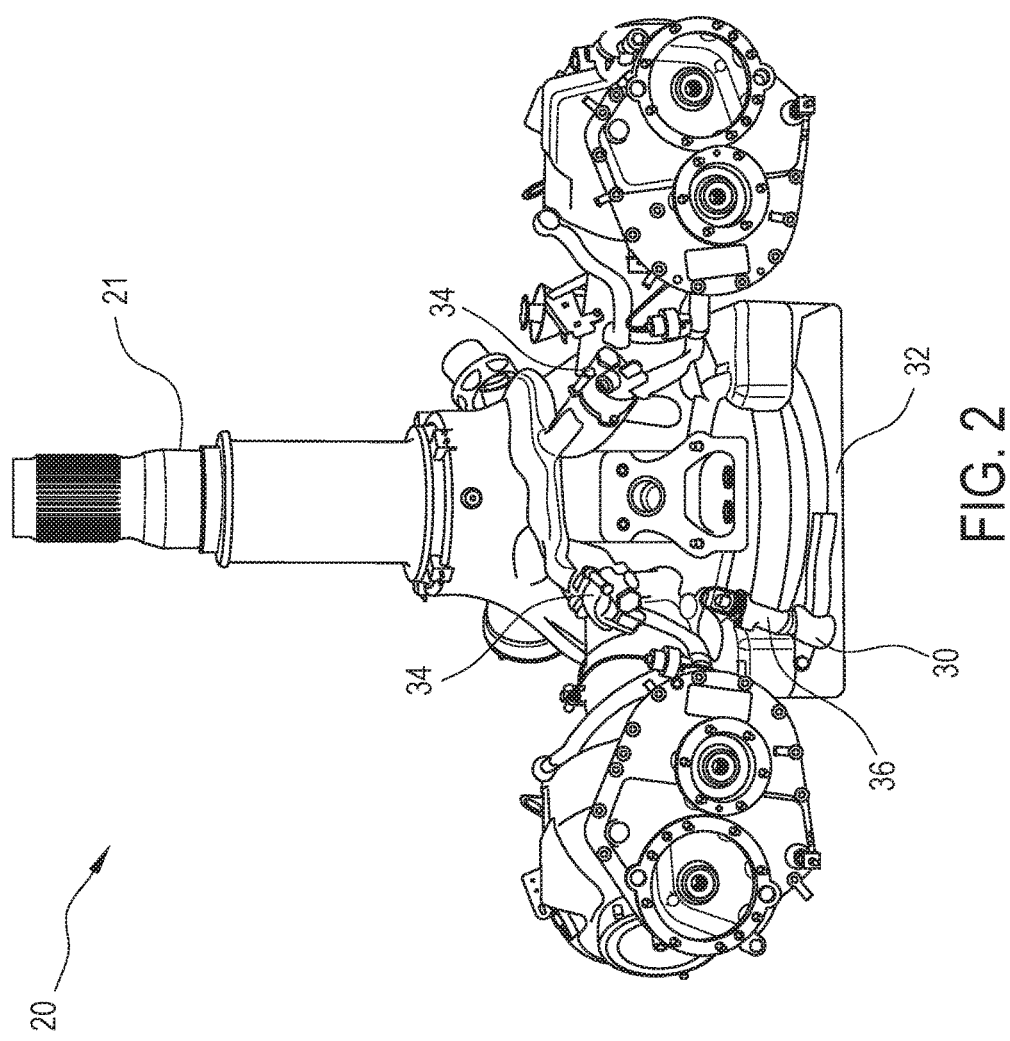
FIG. 2 depicts a gearbox and rotor shaft in an exemplary embodiment.

FIG. 2 depicts a gearbox assembly 20 and main rotor shaft 21 in an exemplary embodiment. A fluid (e.g., lubricant) distribution assembly 30 is positioned in a lubricant sump 32. Lubricant pumps 34 draw lubricant (e.g., oil) from the sump 32, through the lubricant distribution assembly 30 and supply lubricant to gearbox assembly 20. A chip detector assembly 36 may be mounted to the lubricant distribution assembly 30. While described as a lubricant in the context of gearbox assembly 20, it is understood that, in other aspects, the lubricant is only one type of fluid usable with embodiments of the invention. By way of example, the fluid could be fuel where the sump 32 is a gas tank and the fluid distribution assembly 30 distributes fuel to an engine. By way of another example, the fluid could be coolant where the sump 32 is a coolant reservoir and the fluid distribution assembly 30 distributes coolant to cool an engine. Further, while shown with two pumps 34, it is understood that a single pump 34, or other numbers of pumps 34 could be used in other aspects.

Figure 3:
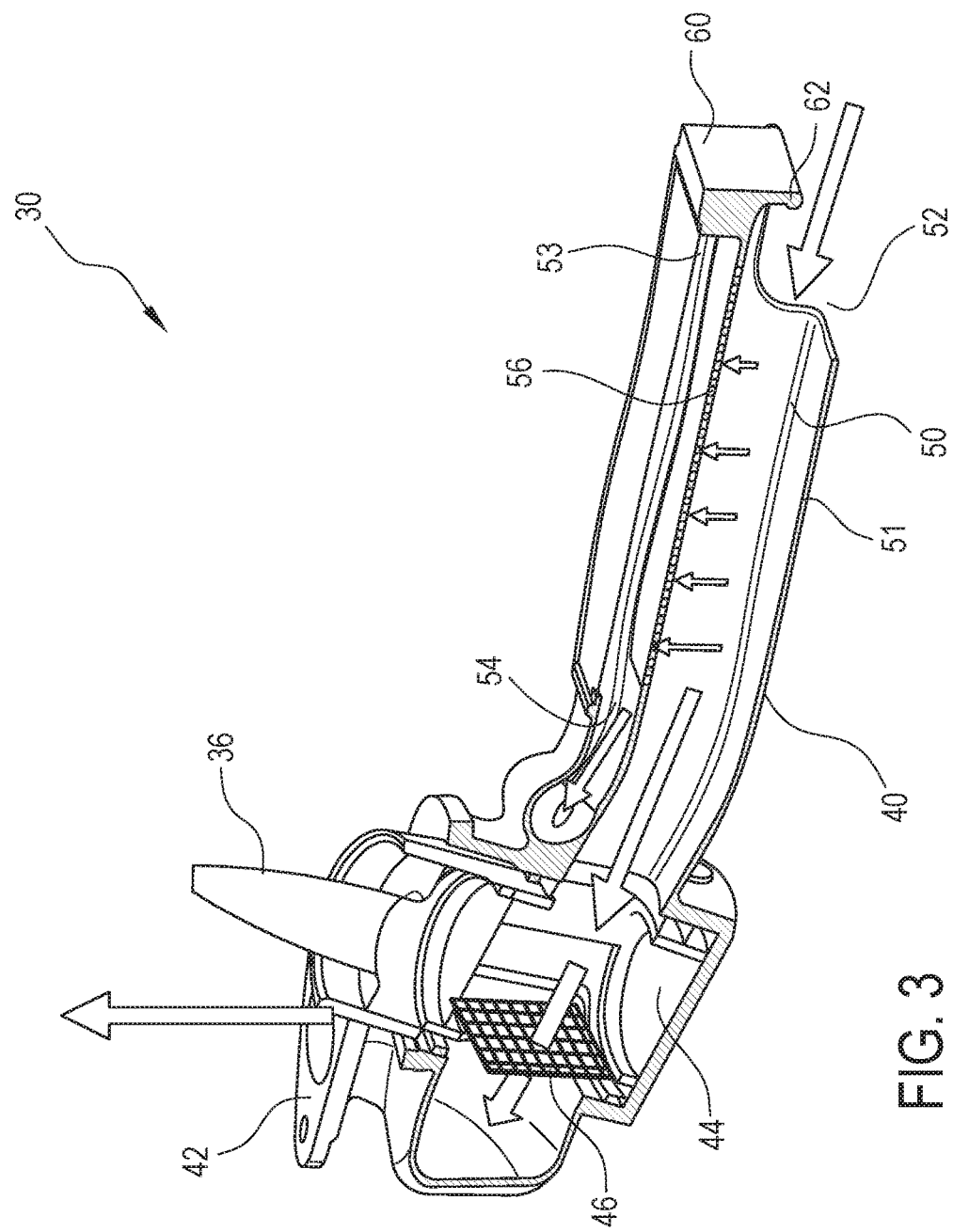
FIG. 3 depicts a lubricant distribution assembly with a first fluid path unblocked in an exemplary embodiment.

FIG. 3 depicts a lubricant distribution assembly 30 in an exemplary embodiment. Lubricant distribution assembly 30 includes an inlet housing 40. Inlet housing 40 is a hollow member for placement in the sump 32 (See FIG. 2). The inlet housing 40 is in fluid communication with an outlet housing 42. An outlet of outlet housing 42 is in fluid communication with the lubricant pump(s) 34 (See FIG. 2). Interposed between inlet housing 40 and outlet housing 42 is a chip detector cavity 44 in fluid communication with inlet housing 40 and outlet housing 42. Chip detector cavity 44 is a generally cylindrical member, having a hollow interior to receive a portion of chip detector assembly 36. A filter 46 captures contaminants in lubricant traveling from the inlet housing 40 to the outlet housing 42. Lubricant traveling from the inlet housing 40 to the outlet housing 42 passes through filter 46. Filter 46 may be implemented using a metal screen or other filter media. Filter 46 may be part of the chip detector assembly 36.

Inlet housing 40 includes a first conduit 50 fluidly coupled to the chip detector cavity 44. First conduit 50 is part of a first fluid path including an inlet 52, first conduit 50, chip detector cavity 44, and outlet housing 42. Inlet housing 40 also includes a bypass conduit 54 extending from inlet 52 to outlet housing 42. Bypass conduit 50 is part of a bypass fluid path including inlet 52, bypass conduit 54, and outlet housing 42. A screen 56 is positioned between first conduit 50 and bypass conduit 54, and allows fluid flow between the first conduit 50 and bypass conduit 54. Screen 56 may be implemented using a metal screen or other filter media. Screen 56 may have the same or a different porosity as filter 46. Bypass conduit 54 allows fluid to bypass the chip detector cavity 44 and filter 46. As shown, the screen 56 is relatively large as compared to filter 46, and extends substantially along a length of the connection between the bypass conduit 54 and the inlet 52 and having a same width as the connection. The screen 46 acts to prevent chips from flowing into the bypass conduit 54 while also allowing sufficient lubricant from flowing through the bypass conduit 54 when there is a blocked condition as described below. However, it is understood that other geometries for the screen 56 can be used.

FIG. 3 depicts lubricant flow in the lubricant distribution assembly 30 with the first fluid path unblocked. Blocked, as used herein, refers to a condition where the flow of lubricant through the first fluid path is below a threshold. During unblocked operation, some lubricant also flows in the bypass fluid path, that is, through bypass conduit 54 and around the chip detector assembly 36. In an exemplary embodiment, about 60% of the lubricant flows in the first fluid path and 40% of the lubricant flows in the bypass fluid path, in an unblocked condition.

Figure 4:
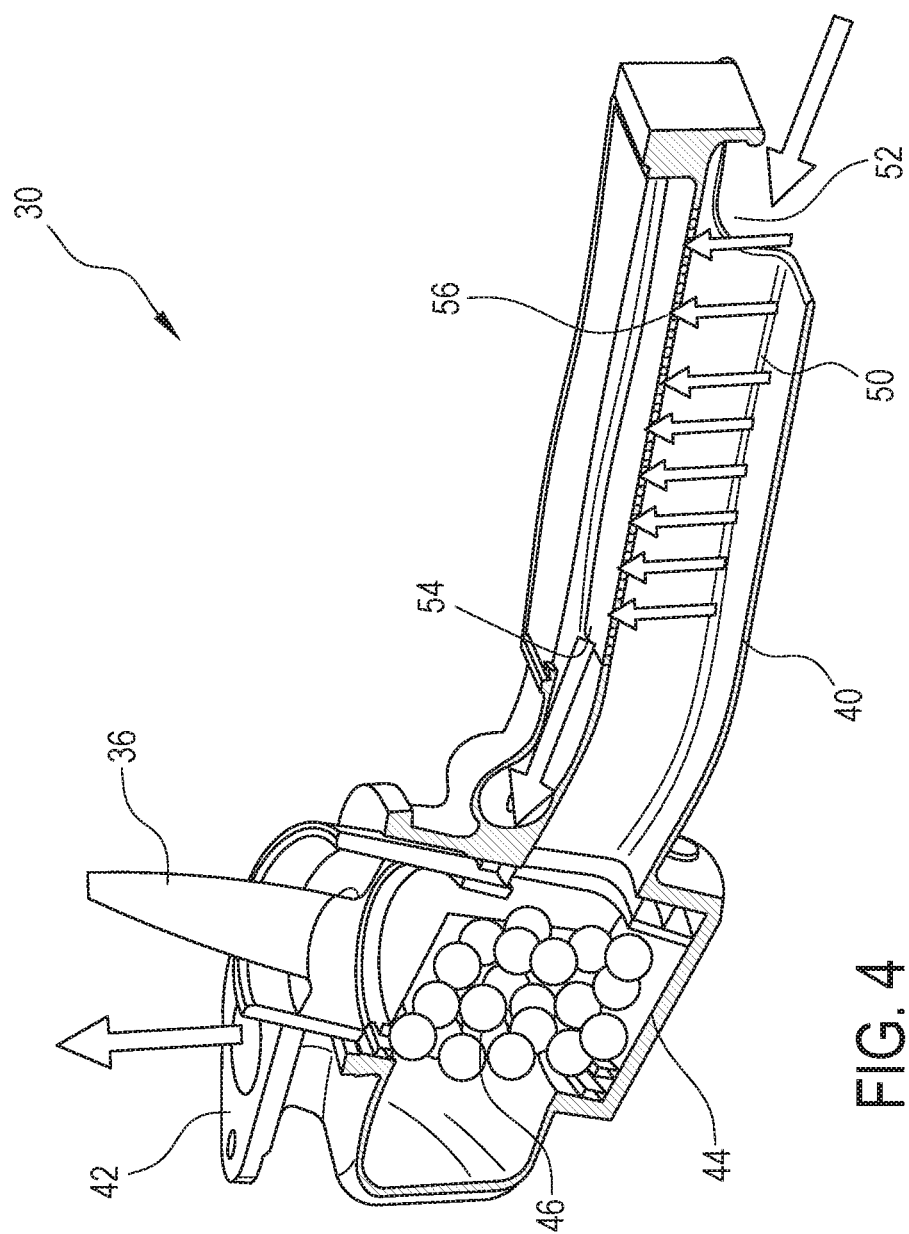
FIG. 4 depicts the lubricant distribution assembly with the first fluid path blocked in an exemplary embodiment.

FIG. 4 depicts the lubricant flow in the lubricant distribution assembly 30 with the first fluid path blocked. This blocked condition may be due to a buildup of debris on filter 46, by way of example. The blocked condition does not require complete blockage or total interruption of lubricant flow in first fluid path. The blocked condition may also be a result of debris buildup in the first conduit 50.

Figure 5:
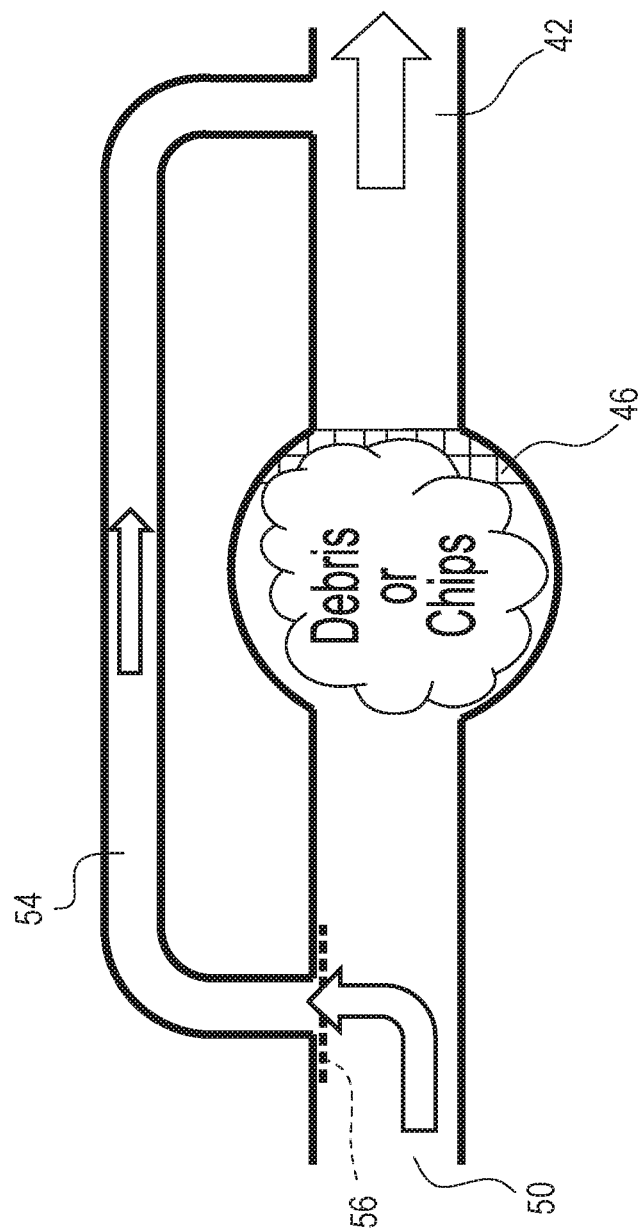
FIG. 5 depicts lubricant flow in the lubricant distribution assembly with the first fluid path blocked in an exemplary embodiment.

During blocked operation of FIG. 4, lubricant enters inlet 52, passes through screen 56, along bypass conduit 54 and to outlet housing 42. The amount of lubricant flow through bypass conduit 54 may be below a certain level, such that a low pressure signal is generated by a lubricant monitoring system in the aircraft. FIG. 5 depicts lubricant flow when the first fluid path is blocked. Lubricant enters first conduit 50, passes through screen 56, through bypass conduit 54 and to outlet housing 42.

Referring to FIG. 3, the inlet housing 40 includes a vortex reducer 60 located adjacent the inlet 52. Inlet 52 is located on a bottom wall 51 of the inlet housing 40. Vortex reducer 60 includes a lip 62, extending downwardly from a top wall 53 of the inlet housing 40. Lip 62 terminates prior to bottom wall 51. Lip 62 serves to disrupt a vortex formed in the lubricant.

Embodiments of the lubricant distribution assembly provide a bypass fluid path to an outlet housing in the event first fluid path is blocked. During normal, unblocked operation, lubricant flows through the chip detector assembly 36 to allow for chip detection. When lubricant pumps 34 are shut off, lubricant flows from outlet housing 42 back to inlet 52, and passes through screen 56. This reverse flow of lubricant removes particles from screen 56. During unblocked or blocked operation, particles in the lubricant are trapped by screen 56, thereby reducing the debris that travels to screen 46 and reducing the likelihood of clogging screen 46. If the first fluid path is blocked, the bypass fluid path provides a restricted flow rate which will result in low fluid pressure indication to the operator of the aircraft.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions, or equivalent arrangement not hereto described will be apparent to those of ordinary skill in the art without departing from the scope and spirit of the invention. By way of example, while described in terms of use on an aircraft, aspects can be used in automobiles, other types of aircrafts beyond rotorcraft, ships, industrial machinery, pipelines, septic or sewer systems, or any other system where fluid flow needs to be maintained. Additionally, while various embodiment of the invention have been described, it is to be understood that aspects of the invention may include only some of the described embodiments. Accordingly, the invention is not to be seen as limited by the foregoing description, but is only limited by the scope of the appended claims.

What is claimed is:

1. A fluid distribution assembly for distributing a fluid, the fluid distribution assembly comprising:
   an inlet housing including a first conduit and a bypass conduit including an inlet portion and an outlet portion;
   a chip detector cavity in fluid communication with the first conduit such that the fluid can pass through the first conduit into the chip detector cavity;
   a screen provided at one of the inlet portion and the outlet portion of the bypass conduit; and
   an outlet housing in fluid communication with the chip detector cavity and the bypass conduit such that the fluid can pass into the outlet housing through the chip detector cavity and through the screen into the bypass conduit in a first direction and fluid may pass in a second, opposing direction from the outlet housing through the bypass conduit back through the screen.

2. The fluid distribution assembly of claim 1 further comprising:
   a screen positioned between the first conduit and the bypass conduit, the screen to pass fluid between the first conduit and the bypass conduit.

3. The fluid distribution assembly according to claim 1 further comprising:
   a filter in the chip detector cavity between the first conduit and the outlet housing.

4. The fluid distribution assembly according to claim 1 wherein:
   when fluid flow through the first conduit and the chip detector cavity is unblocked, fluid flows in the first conduit, the chip detector cavity and the bypass conduit to the outlet housing.

5. The fluid distribution assembly according to claim 1 wherein:
   when fluid flow through the first conduit or the chip detector cavity is blocked, fluid flows in the bypass conduit to the outlet housing.

6. The fluid distribution assembly according to claim 1 wherein: the inlet housing includes an inlet;
   the inlet housing including a vortex reducer located adjacent the inlet which can reduce vortices created at an opening between the first conduit and the bypass conduit.

7. The fluid distribution assembly of claim 6 wherein:
   the vortex reducer includes a lip extending from one wall of the inlet housing towards the inlet.

8. A rotary wing aircraft comprising: a rotor;
   a gearbox coupled to the rotor;
   an engine coupled to the gearbox; and
   a lubricant distribution system providing lubricant from a sump to the gearbox, the lubricant distribution system including:
   an inlet housing including a first conduit and a bypass conduit including an inlet portion and an outlet portion;
   a chip detector cavity in fluid communication with the first conduit such that the fluid can pass through the first conduit into the chip detector cavity, the chip detector cavity housing a chip detector;
   a screen provided at one of the inlet portion and the outlet portion of the bypass conduit; and
   an outlet housing in fluid communication with the chip detector cavity and the bypass conduit such that the fluid can pass into the outlet housing through the chip detector cavity and through the screen into the bypass conduit in a first direction and fluid may pass in a second, opposing direction from the outlet housing through the bypass conduit back through the screen.

9. The rotary wing aircraft of claim 8 further comprising:
   a screen positioned between the first conduit and the bypass conduit, the screen passing fluid between the first conduit and the bypass conduit.

10. The rotary wing aircraft according to claim 8 further comprising:
    a filter in the chip detector cavity between the first conduit and the outlet housing.

11. The rotary wing aircraft according to claim 8 wherein:
    when fluid flow through the first conduit is unblocked, fluid flows in the first conduit and the bypass conduit to the outlet housing.

12. The rotary wing aircraft according to claim 8 wherein:
    when fluid flow through the first conduit is blocked, fluid flows in the bypass conduit to the outlet housing.

13. The rotary wing aircraft according to claim 8 wherein:
    the inlet housing includes an inlet;
    the inlet housing including a vortex reducer located adjacent the inlet.

14. The rotary wing aircraft of claim 13 wherein:
    the vortex reducer includes a lip extending from one wall of the inlet housing towards the inlet.

15. The rotary wing aircraft according to claim 8 further comprising:
    a pump coupled to the outlet housing, the pump directing lubricant through inlet housing.

* * * * *